DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED NOVEMBER 23, 1971

892 O.G. 1210

T892,007
METHOD FOR PREPARING THALLOUS ETHOXIDE

Thomas M. Gormel, 1669 Lake Ave., Rochester, N.Y. 14650

Filed Oct. 29, 1970, Ser. No. 85,304
Int. Cl. C07j *5/00*
U.S. Cl. 260—429 R
No Drawing. 7 Pages Specification

Thallous ethoxide is prepared by the reaction of an alkali metal ethoxide with thallous nitrate or thallous sulfate in ethanol. The alkali metal can be sodium potassium or lithium. The reactants can be dissolved in ethanol and the solution heated at reflux temperature. Alternatively the alkali metal ethoxide can be formed in situ as by adding the alkali metal or its hydroxide to an excess of hot ethanol, the thallous nitrate or sulfate then is added, and the solution is heated at reflux temperature. Time of heating at reflux can be 6 to 48 hours, preferably 24 to 48 hours. The product is then recovered by filtration followed by recovery of product from the filtrate in a separatory funnel.